(12) United States Patent  (10) Patent No.: US 7,594,344 B2
Mizrahi  (45) Date of Patent: Sep. 29, 2009

(54) AROMATHERAPY FOOTWEAR

(76) Inventor: Hagay Mizrahi, 4551 Larkwood Ave., Woodland Hills, CA (US) 91364

( * ) Notice: Subject to any disclaimer, the term of this patent is extended or adjusted under 35 U.S.C. 154(b) by 600 days.

(21) Appl. No.: 11/524,871

(22) Filed: Sep. 21, 2006

(65) Prior Publication Data

US 2008/0072451 A1    Mar. 27, 2008

(51) Int. Cl.
  *A43B 7/02*    (2006.01)
  *A43B 3/24*    (2006.01)
(52) U.S. Cl. ............................... 36/2.6; 36/101; 36/9 R
(58) Field of Classification Search ................ 36/2.6, 36/101, 100, 15, 9 R
  See application file for complete search history.

(56) References Cited

U.S. PATENT DOCUMENTS

| | | |
|---|---|---|
| 520,417 A | 5/1894 | Foss |
| 1,030,085 A | 6/1912 | Hale |
| 1,286,446 A | 12/1918 | Thoma, Jr. |
| 1,663,376 A | 3/1928 | Koller |
| 1,735,434 A | 11/1929 | Hohenstein |
| 1,753,415 A | 4/1930 | Hepburn |
| 2,205,091 A | 6/1940 | Geffner |
| 2,675,630 A | 4/1954 | Youmans |
| 2,680,918 A | 6/1954 | Behner |
| 3,693,270 A | 9/1972 | Murray |
| 4,023,282 A | 5/1977 | Ziegelheafer |
| 4,094,080 A | 6/1978 | Sanders |
| 4,726,126 A | 2/1988 | Bernhard |
| 4,800,867 A | 1/1989 | Owens |
| 4,813,162 A | 3/1989 | Harris |
| 4,841,646 A | 6/1989 | Maurer, Jr. |
| 5,230,170 A | 7/1993 | Dahle |
| 5,339,541 A | 8/1994 | Owens |
| 5,357,693 A | 10/1994 | Owens |
| 5,476,492 A | 12/1995 | Unrug |
| 6,094,844 A | 8/2000 | Potts |
| 6,532,689 B1 | 3/2003 | Jones, Jr. |
| 6,576,003 B2 * | 6/2003 | Kotack ...................... 36/2.6 |
| 6,701,639 B2 | 3/2004 | Treptow et al. |
| 6,855,410 B2 | 2/2005 | Buckley |
| 6,891,078 B1 | 5/2005 | Dillard |
| 6,920,707 B1 | 7/2005 | Greene et al. |
| 6,991,842 B2 | 1/2006 | Hurwitz |
| 7,010,869 B1 | 3/2006 | Ellis, III |
| 7,010,872 B2 | 3/2006 | Pawlus et al. |
| 7,028,417 B2 | 4/2006 | Tingle |
| 7,484,318 B2 * | 2/2009 | Finkelstein ................ 36/44 |

(Continued)

*Primary Examiner*—Ted Kavanaugh
(74) *Attorney, Agent, or Firm*—David A. Belasco; Belasco Jacobs & Townsley, LLP

(57) ABSTRACT

An aromatherapy footwear includes a lower portion and an upper portion formed of resilient material sized and shaped to fit beneath and above a foot of a user. The upper portion is hingedly attached to the lower portion. An aromatherapy pouch is formed of flexible, aroma-permeable material and sized and shaped to fit beneath the foot above the lower portion. The pouch contains aromatherapy and thermal reservoir materials. A cavity is located between the upper portion and the lower portion and is sized and shaped to receive the aromatherapy pouch. Stitching through the aromatherapy pouch at least partially divides the compartment into at least two subspaces to control movement of the contents. When the aromatherapy pouch is heated or cooled and placed in the cavity the footwear will heat or cool while providing aromatherapy benefits. The footwear includes an outer sole formed of resilient material and suitable for outdoor use.

15 Claims, 2 Drawing Sheets

U.S. PATENT DOCUMENTS

| | | |
|---|---|---|
| 2003/0009138 A1 | 1/2003 | Freeman et al. |
| 2005/0210704 A1* | 9/2005 | Connolly ..................... 36/2.6 |
| 2006/0010717 A1* | 1/2006 | Finkelstein ................ 36/25 R |
| 2006/0053654 A1 | 3/2006 | Tingle |
| 2009/0094855 A1* | 4/2009 | Finkelstein ................... 36/28 |

* cited by examiner

AROMATHERAPY FOOTWEAR

FIELD OF INVENTION

The invention pertains to devices for alleviating muscle soreness, fatigue and stress. More particularly, the invention relates to removable packs containing thermal retention and aromatherapy materials that can be heated or cooled and then applied to the feet in compartmentalized slippers to provide relief through temperature difference and aromatherapy related to the herbs contained in the pack.

BACKGROUND OF THE INVENTION

Heating and cooling pads in various form a have long been in use for alleviating soreness, stiffness, aching muscles and the results of various types of injuries. Likewise, aromatherapy products have been in use in Eastern cultures for hundreds of years and are now achieving prominence in the West. The combination of heating and cooling devices with aromatherapy products has served to provide increased benefits for those with muscle, tendon and joint problems. A number of inventions have been developed that use one or more of these components to alleviate pain or soreness.

U.S. Patent Application No 2003/0009138, published for Freeman et al., discloses footwear and footwear components including insole pads, inserts and liners containing plant-derived essential oils and/or dried plant products applied to or constructed within the footwear and footwear components to deliver the comfort, disinfectant and/or therapeutic benefits of aromatherapy through direct contact with the wearer's feet with the volatile components of the plant derived oils and/or plant products.

U.S. Pat. No. 6,991,842, issued to Hurwitz describes a scent dispersing apparatus, such as a mat, capable of enclosing a scent-containing element inside an air-filled cavity. A housing contains a means for air ventilation, such as small air holes, for dispersion of scent. When the housing receives a force, such as a user exerting pressure upon on the housing, air is pushed from the air cavity outward through the air holes, thereby, dispersing scent contained in the scented insert. Additional air enters the air cavity once the pressure is released through an elastic rebound effect.

U.S. Pat. No. 7,028,417, issued to Tingle discloses a footwear article for slidably receiving a foot, the slipper having a sole, a vamp panel joined to the sole, a toe panel disposed over the vamp panel, a front toe pocket, a quarter panel joined to the sole and at least one rear pocket. The vamp portion is disposed over the toes and covers a lower instep of the foot; the quarter panel covers the sides of the foot, the heel, and the ankle region. The slipper may be used alone or in conjunction with a removably attachable instep panel, having an instep pocket. When the slipper is used with the instep panel, the entire foot is covered and the entire ankle encircled. The front toe pocket, the rear pocket and the instep pocket are designed to receive therapeutic devices that will disseminate a particular effect over different regions of the foot and help relieve foot pain.

U.S. Pat. No. 4,813,162, issued to Harris describes a device for receiving an orthotic insert of a predetermined configuration is disclosed. The device comprises a sheath comprised of a substantially flexible material having a first end and a second end, and two opposed outer surfaces. An opening is provided at one of the opposed outer surfaces near the first end. The two opposed inner surfaces define an inner pocket therebetween which is in communication with the opening. The inner pocket has dimensions and a volume sufficient to accommodate the orthotic insert.

U.S. Pat. No. 6,532,689, issued to Jones, Jr., describes a slipper which has an aperture in the bottom and three different types of inserts which can be inserted into the aperture. The first insert will be filled with a material that conforms to the wearer's foot, while the second insert will be filled with a mixture of sand and marbles. The third insert will be filled with neoprene balls.

U.S. Pat. No. 5,357,693, issued to Owens, discloses a therapeutic pad is used in footwear which has a liquid absorbent to prevent liquid leakage in the event the sealed envelope of the pad is ruptured. The footwear includes a pair of compartments which substantially surround the foot cavity for receiving the therapeutic pad.

It is an objective of the present invention to provide a means to alleviate muscle soreness, cramps, aches and pains, etc. in the feet without the use of drugs or invasive procedures. It is a further objective to provide therapeutic heating or cooling to the feet in portable devices that allow the user to walk about comfortably. It is a still further objective of the invention to provide comfortable footwear having therapeutic aromatherapy effects that can be worn out of doors. Finally, it is an objective of the invention to provide slippers or shoes with the above benefits that can use interchangeable thermal and aromatherapy packs.

While some of the objectives of the present invention are disclosed in the prior art, none of the inventions found include all of the requirements identified.

SUMMARY OF THE INVENTION

The present invention addresses all of the deficiencies of therapeutic footwear inventions and satisfies all of the objectives described above.

(1) Aromatherapy footwear, providing all of the desired features can be constructed from the following components. A lower portion is provided. The lower portion is formed of resilient material and sized and shaped to fit beneath a foot of a user. An upper portion is provided. The upper portion is formed of resilient material, sized and shaped to surround at least a portion of the foot, and is hingedly attached to the lower portion. An aromatherapy pouch is provided. The pouch is formed of flexible, aroma-permeable material. It is sized and shaped to fit beneath the foot above the lower portion and contains aromatherapy materials and thermal reservoir materials. A cavity is provided. The cavity is located between the upper portion and the lower portion and is sized and shaped to receive the aromatherapy pouch. When the aromatherapy pouch is heated or cooled and placed in the cavity and the footwear is placed upon the foot, the footwear will heat or cool the foot while providing aromatherapy benefits.

(2) In a variant of the invention, the aromatherapy pouch includes a top panel and a bottom panel. The panels are joined at their peripheral edges and form a compartment enclosing the aromatherapy materials and thermal reservoir materials.

(3) In another variant, the aromatherapy pouch further includes stitching. The stitching at least partially divides the compartment into at least two subspaces.

(4) In yet another variant, at least two of the subspaces are interconnected, thereby permitting the thermal reservoir materials and the aromatherapy materials to move between the subspaces.

(5) In still another variant, the lower portion includes an outer sole. The outer sole is formed of resilient material and suitable for outdoor use.

(6) In a further variant, the footwear includes a footpad. The footpad is formed of resilient material and sized and shaped to fit between the lower portion and the aromatherapy pouch.

(7) In still a further variant, the aromatherapy pouch includes at least one retaining pocket. The retaining pocket is sized and shaped to fit slidably over an end of the footpad, thereby preventing movement of the aromatherapy pouch within the footwear.

(8) In yet a further variant, the upper portion includes a barrier layer. The barrier layer is formed of aroma-permeable material and is joined to a lower peripheral edge of the upper portion, thereby providing an aroma permeable insulating layer between the aromatherapy pouch and the foot.

(9) In another variant of the invention, the upper portion is hingedly attached to the lower portion by means selected from the group consisting of zippers, snaps, buttons and hook and loop fasteners.

(10) In yet another variant, the upper portion is removably attached to the lower portion.

(11) In still another variant, the upper portion is lined with insulating material.

(12) In a further variant, the thermal reservoir materials are selected from the group consisting of corn, rice, wheat, oats, barley, beans and flaxseed.

(13) In still a further variant, the aromatherapy materials are selected from the group consisting of cinnamon, chamomile, lemongrass, peppermint, rosemary, spearmint, valerian root, white willow, yarrow, lavender ginger and yellow dock root.

(14) In yet a further variant, the compartment has at least one openable closure to permit introduction of alternative thermal and aromatherapy materials.

(15) In a final variant of the invention, the openable closures are selected from the group consisting of hook and loop fastener, zipper, button and tie string.

An appreciation of the other aims and objectives of the present invention and an understanding of it may be achieved by referring to the accompanying drawings and the detailed description of a preferred embodiment.

DESCRIPTION OF THE DRAWINGS

DETAILED DESCRIPTION OF THE PREFERRED EMBODIMENT (1) FIGS. 1-4 illustrate aromatherapy footwear 10, providing all of the desired features that can be constructed from the following components. A lower portion 14 is provided. The lower portion 14 is formed of resilient material and sized and shaped to fit beneath a foot (not shown) of a user. An upper portion 22 is provided. The upper portion 22 is formed of resilient material, sized and shaped to surround at least a portion of the foot, and is hingedly attached to the lower portion 14. An aromatherapy pouch 26 is provided. The pouch 26 is formed of flexible, aroma-permeable material. It is sized and shaped to fit beneath the foot above the lower portion 14 and contains aromatherapy materials 30 and thermal reservoir materials 34. A cavity 38 is provided. The cavity 38 is located between the upper portion 22 and the lower portion 14 and is sized and shaped to receive the aromatherapy pouch 26. When the aromatherapy pouch 26 is heated or cooled and placed in the cavity 38 and the footwear 10 is placed upon the foot, the footwear 10 will heat or cool the foot while providing aromatherapy benefits.

Figure 2:
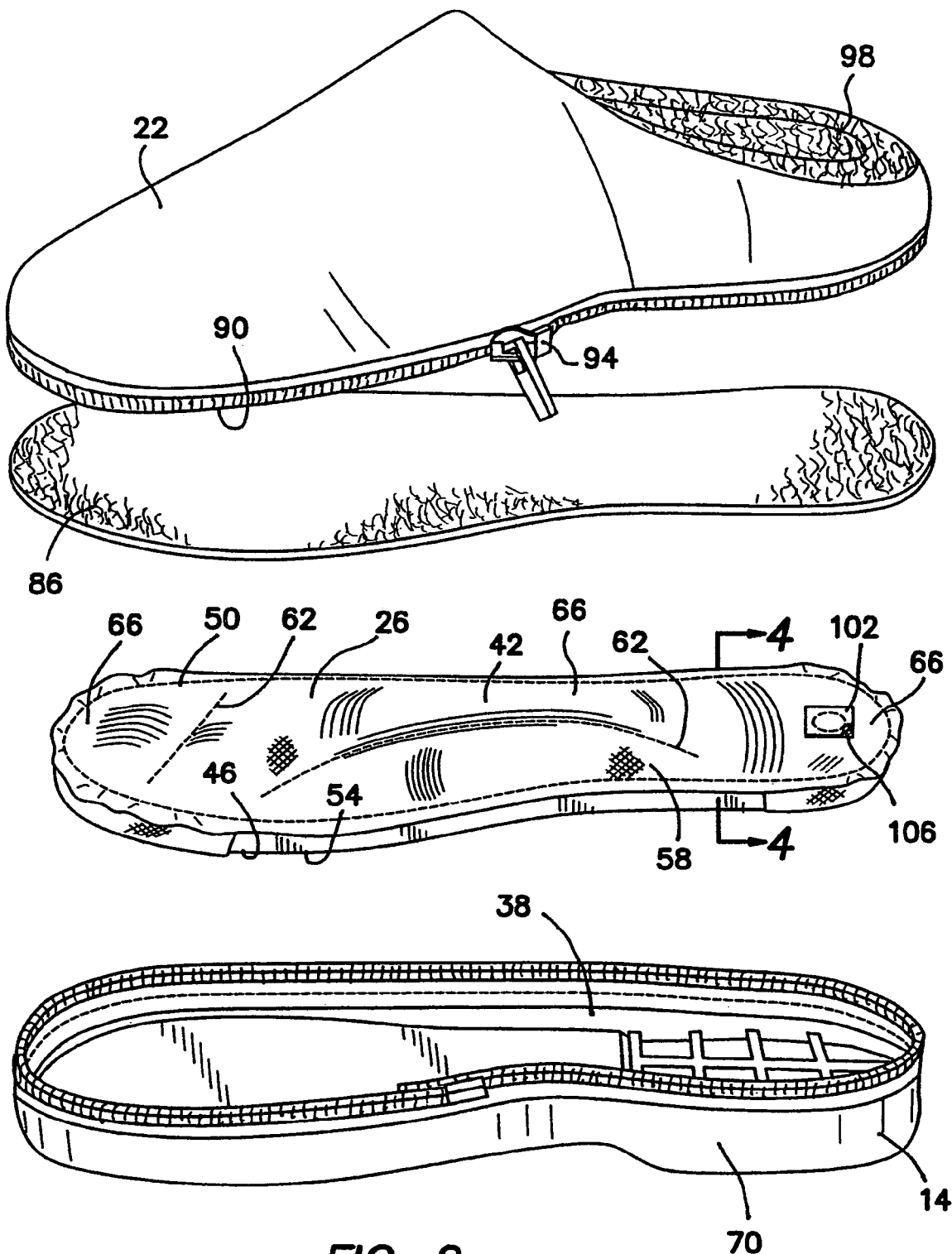
FIG. 2 is perspective view of the FIG. 1 embodiment in disassembled form illustrating the upper, the barrier layer, the aromatherapy pouch, the footpad and the lower portion of the footwear.

(2) In a variant of the invention, as illustrated in FIG. 2, the aromatherapy pouch 26 includes a top panel 42 and a bottom panel 46. The panels 42, 46 are joined at their peripheral edges 50, 54 and form a compartment 58 enclosing the aromatherapy materials 30 and thermal reservoir materials 34.

(3) In another variant, the aromatherapy pouch 26 further includes stitching 62. The stitching 62 at least partially divides the compartment 58 into at least two subspaces 66.

(4) In yet another variant, at least two of the subspaces 66 are interconnected, thereby permitting the thermal reservoir materials 30 and the aromatherapy materials 34 to move between the subspaces 66.

(5) In still another variant, the lower portion 14 includes an outer sole 70. The outer sole 70 is formed of resilient material and suitable for outdoor use.

Figure 1:
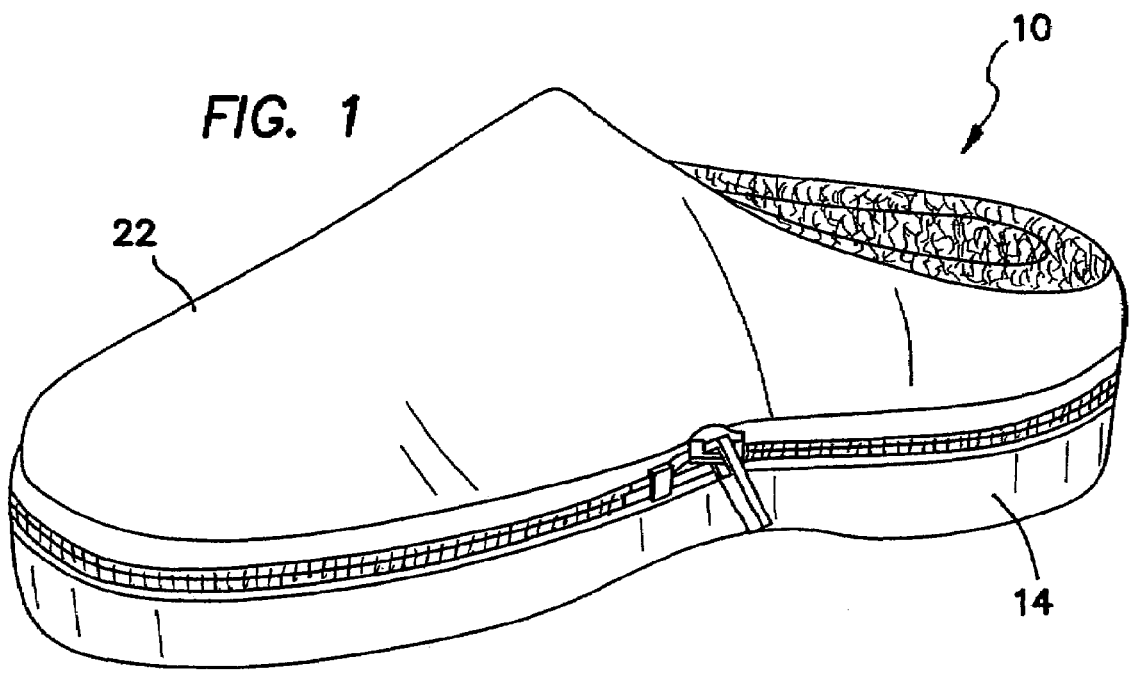
FIG. 1 is a perspective view of the preferred embodiment of the invention.
Figure 3:
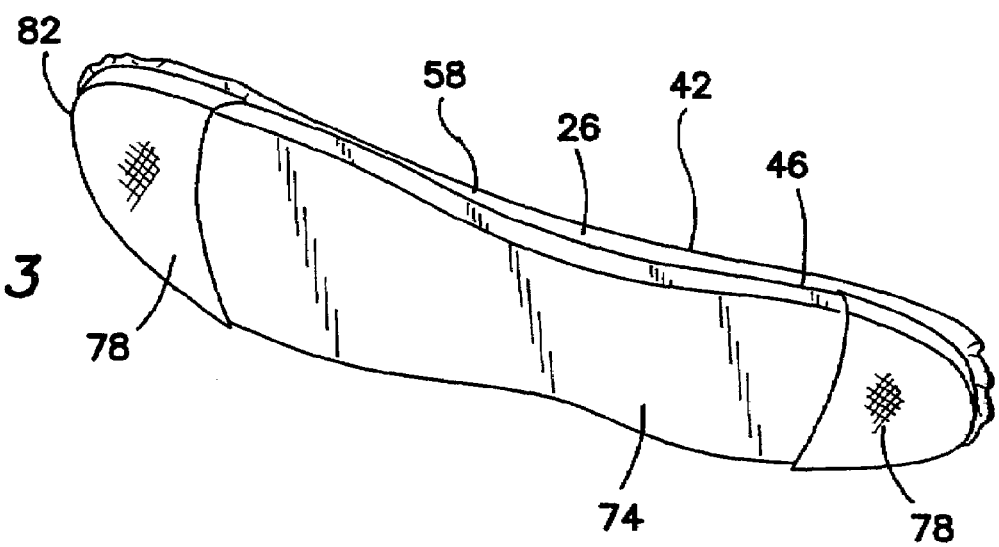
FIG. 3 is a perspective view of the aromatherapy pouch as seen from below, illustrating the retaining pockets holding the pouch to the footpad.
Figure 4:
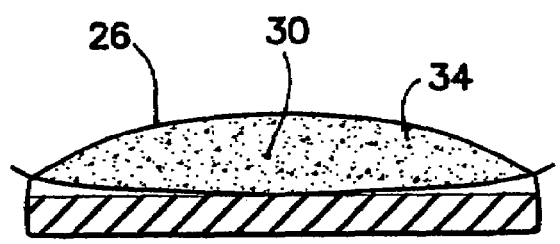
FIG. 4 is a cross-sectional view of the aromatherapy pouch and the footpad taken along the line 4-4.

(6) In a further variant, as illustrated in FIGS. 2 and 3, the footwear 10 includes a footpad 74. The footpad 74 is formed of resilient material and sized and shaped to fit between the lower portion 14 and the aromatherapy pouch 26.

(7) In still a further variant, the aromatherapy pouch 26 includes at least one retaining pocket 78. The retaining pocket 78 is sized and shaped to fit slidably over an end 82 of the footpad 74, thereby preventing movement of the aromatherapy pouch 26 within the footwear 10.

(8) In yet a further variant, as illustrated in FIG. 2, the upper portion 22 includes a barrier layer 86. The barrier layer 86 is formed of aroma-permeable material and is joined to a lower peripheral edge 90 of the upper portion 22, thereby providing an aroma permeable insulating layer between the aromatherapy pouch 26 and the foot.

(9) In another variant of the invention, the upper portion 22 is hingedly attached to the lower portion 14 by means selected from the group consisting of zippers 94, snaps (not shown), buttons (not shown) and hook and loop fasteners (not shown).

(10) In yet another variant, the upper portion 22 is removably attached to the lower portion 14.

(11) In still another variant, the upper portion 22 is lined with insulating material 98.

(12) In a further variant, the thermal reservoir materials 34 are selected from the group consisting of corn, rice, wheat, oats, barley, beans and flaxseed.

(13) In still a further variant, the aromatherapy materials 30 are selected from the group consisting of cinnamon, chamomile, lemongrass, peppermint, rosemary, spearmint, valerian root, white willow, yarrow, lavender ginger and yellow dock root.

(14) In yet a further variant, the compartment 58 has at least one openable closure 102 to permit introduction of alternative thermal 34 and aromatherapy 30 materials.

(15) In a final variant of the invention, the openable closures 102 are selected from the group consisting of hook and loop fastener 106, zipper (not shown), button (not shown) and tie string (not shown).

The aromatherapy blanket 10 has been described with reference to particular embodiments. Other modifications and enhancements can be made without departing from the spirit and scope of the claims that follow.

The invention claimed is:

1. Aromatherapy footwear, comprising:
   a lower portion, said lower portion being formed of resilient material and sized and shaped to fit beneath a foot of a user;
   an upper portion, said upper portion being formed of resilient material, sized and shaped to surround at least a portion of said foot, and being hingedly attached to said lower portion;
   an aromatherapy pouch, said pouch being formed of flexible, aroma-permeable material, sized and shaped to fit beneath said foot above said lower portion and containing aromatherapy materials and thermal reservoir materials;
   a cavity, said cavity being disposed between said upper portion and said lower portion and being sized and shaped to receive said aromatherapy pouch; and
   whereby, when said aromatherapy pouch is heated or cooled and placed in said cavity and said footwear is placed upon said foot, said footwear will heat or cool said foot while providing aromatherapy benefits.

2. The aromatherapy footwear, as described in claim 1, wherein said aromatherapy pouch further comprises a top panel and a bottom panel, said panels being joined at their peripheral edges and forming a compartment enclosing said aromatherapy materials and thermal reservoir materials.

3. The aromatherapy footwear, as described in claim 2, wherein said compartment has at least one openable closure to permit introduction of alternative thermal and aromatherapy materials.

4. The aromatherapy footwear, as described in claim 3, wherein said openable closures are selected from the group consisting of:
   hook and loop fastener, zipper, button and tie string.

5. The aromatherapy footwear, as described in claim 2, further comprising stitching, said stitching at least partially dividing said compartment into at least two subspaces.

6. The aromatherapy footwear, as described in claim 5, wherein at least two of said subspaces are interconnected, thereby permitting said thermal reservoir materials and said aromatherapy materials to move between said subspaces.

7. The aromatherapy footwear, as described in claim 1, wherein said lower portion further comprises an outer sole, said outer sole being formed of resilient material and suitable for outdoor use.

8. The aromatherapy footwear, as described in claim 1, further comprising a footpad, said footpad being formed of resilient material and sized and shaped to fit between said lower portion and said aromatherapy pouch.

9. The aromatherapy footwear, as described in claim 8, wherein said aromatherapy pouch further comprises at least one retaining pocket, said retaining pocket being sized and shaped to fit slidably over an end of said footpad, thereby preventing movement of said aromatherapy pouch within said footwear.

10. The aromatherapy footwear, as described in claim 1, wherein said upper portion further comprises a barrier layer, said barrier layer being formed of aroma-permeable material and being joined to a lower peripheral edge of said upper portion, thereby providing an aroma permeable insulating layer between said aromatherapy pouch and said foot.

11. The aromatherapy footwear, as described in claim 1, wherein said upper portion is hingedly attached to said lower portion by means selected from the group consisting of:
    zippers, snaps, buttons and hook and loop fasteners.

12. The aromatherapy footwear, as described in claim 1, wherein said upper portion is removably attached to said lower portion.

13. The aromatherapy footwear, as described in claim 1, wherein said upper portion is lined with insulating material.

14. The aromatherapy footwear, as described in claim 1, wherein said thermal reservoir materials are selected from the group consisting of:
    corn, rice, wheat, oats, barley, beans and flaxseed.

15. The aromatherapy footwear, as described in claim 1, wherein said aromatherapy materials are selected from the group consisting of:
    cinnamon, chamomile, lemongrass, peppermint, rosemary, spearmint, valerian root, white willow, yarrow, lavender ginger and yellow dock root.

* * * * *